United States Patent [19]

Talwalker et al.

[11] Patent Number: 5,462,714
[45] Date of Patent: Oct. 31, 1995

[54] ANTIMICROBIAL COMPOSITION AND METHODS OF USE

[75] Inventors: Ramesh T. Talwalker; Shirish S. Barve, both of Lexington, Ky.

[73] Assignee: Arda Technologies, Lexington, Ky.

[21] Appl. No.: 210,523

[22] Filed: Mar. 18, 1994

Related U.S. Application Data

[63] Continuation-in-part of Ser. No. 949,432, Sep. 22, 1992.
[51] Int. Cl.⁶ ............................................. A61K 33/18
[52] U.S. Cl. ................. 422/37; 352/107; 422/28; 424/667
[58] Field of Search ................. 422/27, 28, 37; 424/667, 672; 252/106, 107

[56] References Cited

U.S. PATENT DOCUMENTS

| | | | |
|---|---|---|---|
| 2,739,922 | 3/1956 | Shelanski | 524/548 |
| 3,728,449 | 4/1973 | Cantor et al. | 424/672 X |
| 3,751,565 | 8/1973 | Santorelli | 424/78.6 |
| 3,911,107 | 10/1975 | Krezanoski | 424/667 |
| 4,031,209 | 6/1977 | Krezanoski | 424/672 |
| 4,088,597 | 5/1978 | Morlock et al. | 252/106 |
| 4,128,633 | 12/1978 | Lorenz et al. | 525/358 |
| 4,206,204 | 6/1980 | Langford | 424/672 |
| 4,312,833 | 1/1982 | Clough et al. | 422/30 |
| 4,323,557 | 4/1982 | Rosso et al. | 424/448 |
| 4,404,040 | 9/1983 | Wang | 252/106 X |
| 4,440,947 | 4/1984 | Arlt | 560/226 |
| 4,452,780 | 6/1984 | Ecanow | 424/150 |
| 4,839,080 | 6/1989 | Jungermann et al. | 252/107 |
| 4,844,898 | 7/1989 | Komori et al. | 424/150 |

FOREIGN PATENT DOCUMENTS

| | | |
|---|---|---|
| 0079782 | 5/1983 | European Pat. Off. . |
| 1156904 | 6/1989 | Japan . |

OTHER PUBLICATIONS

Martindale The Extra Pharmacopoeia, 28th ed. London, The Pharmaceutical Press, 1982, pp. 731, 784–785, 865 and 867–868.

*Primary Examiner*—Robert J. Warden
*Assistant Examiner*—Krisanne M. Thornton
*Attorney, Agent, or Firm*—King and Schickli

[57] ABSTRACT

A substantially noncorrosive antimicrobial composition includes by weight percent between 0.25 to 2.0% available iodine, 20.0 to 50.0% fatty acid, 15.0%–35% non-ionic surfactant, 5.0–16.0% (w/v) buffering agent and 10.0–60.0% water (v/v). The composition has a pH between 3.0 and 5.0. Methods for using the composition are also disclosed.

17 Claims, No Drawings

ANTIMICROBIAL COMPOSITION AND METHODS OF USE

This is a continuation-in-part of U.S. patent application Ser. No. 07/949,432 filed Sep. 22, 1992 and entitled "Active Agent Intermediate And Antimicrobial Composition As Well As Method For Preparing The Same"

TECHNICAL FIELD

The present invention relates generally to the sanitizer, disinfectant and antiseptic field.

BACKGROUND OF THE INVENTION

Compositions with antimicrobial properties have long been known in the art. Known antimicrobial agents include: (1) acids, such as, acetic, benzoic, boric, hydrochloric, nitric, phosphoric, sulfuric; (2) alkalis, such as calcium hydroxide, sodium hydroxide, potassium hydroxide, trisodium phosphate, sodium borate, sodium carbonate; (3) aldehydes, such as, acetyl aldehyde, formaldehyde, glyceraldehyde; (4) aromatic oils, such as camphor, cinnamon, peppermint, pine; (5) dyes, such as acridine and malachite green; (6) sulfonamides, such as sulfanilamide, sulfathiazole, sulfapyridine. Additional known antimicrobial agents include: (7) alcohols, such as methyl, ethyl, isopropyl, benzyl; (8) coal-tar derivatives, such as, phenol, para-nitrophenol; (9) reducing agents, such as carbon monoxide, sodium thiosulfate; (10) oxidizing agents, such as, bromine, chorine, iodine, perchloric acid, sodium permanganate; (11) surface active agents, such as anionics (sulfonates), cationics (quaternary ammonium salts), non-ionics (alkylated aryl polyether alcohol); and (12) metal salts of, for example, aluminum, cobalt, copper, iron, mercury, silver and zinc.

These and other antimicrobial agents are used in one form or another in hospitals, eating and drinking establishments, dairies, food processing plants and homes among other places to kill various microorganisms including bacteria, fungi, viruses and protozoans. Particularly, these antimicrobial agents are referred to as disinfectants when applied to inanimate objects to kill microorganisms and antiseptics when applied to living tissue to kill microorganisms.

An ideal antimicrobial agent or composition would rapidly destroy bacteria, fungi, viruses and protozoans, not be corrosive and not destroy or discolor materials on which it is utilized and not be rapidly inactivated by organic matter. Despite advances made through the years in the development of antimicrobial agents and compositions, an ideal agent or composition that would maintain its efficacy in an organic matter environment and destroy all of these organisms without causing any residual toxic side effects is yet to be developed. Accordingly, a need exists for an improved antimicrobial composition more closely meeting the desirable characteristics and properties described.

SUMMARY OF THE INVENTION

Accordingly, it is a primary object of the present invention to provide an improved antimicrobial composition that is relatively easy and inexpensive to produce.

Another object of the present invention is to provide a safe (substantially noncaustic or noncorrosive to both animate and inanimate objects) and effective (retaining its germicidal activity over a wide range of environmental conditions) germicide.

Yet another object of this invention is to provide a novel composition providing enhanced antimicrobial activity so as to be effective against bacteria, fungi, viruses and protozoans even in the presence of organic matter.

Other objects and advantages of the invention will become apparent as the description thereof proceeds. In satisfaction of the foregoing objects and advantages, there is provided by this invention an improved antimicrobial composition. The antimicrobial composition comprises by weight percent substantially 0.25–2.0% available iodine, 20.0–50.0% fatty acid, 15.0–35.0% non-ionic surfactant, 5.0–16.0% (w/v) buffering agent and 10.0–60.0% (v/v) water. Preferably, the pH of the composition is maintained between pH 3.0 and 5.0, more preferably between pH 3.8 and 4.2 and most preferably substantially pH 3.9.

Preferably, the available iodine is provided from an iodophor. Iodophors, of the type described including non-ionic surfactants as carriers, are well-known in the art. Such iodophors typically exhibit enhanced bactericidal activity of iodine, reduced vapor pressures and reduced odor. Additionally, iodophors do not tend to stain and, advantageously, wide dilution with water is possible so that various concentrations of iodophor may be utilized.

The fatty acid is preferably an organic acid selected from a group consisting of formic acid, acetic acid, propionic acid, n-butyric acid, isobutyric acid, n-valeric acid, isovaleric acid, lactic acid, and mixtures thereof.

Additional non-ionic surfactant is utilized beyond that provided in the iodophor. More particularly, sufficient additional non-ionic surfactant is added so as to bring the total concentration up to between 15.0 to 35.0% by weight. This serves to stabilize the composition for the addition of buffering agent so as to allow the pH to be brought to the desired range of between pH 3.0 to 5.0, more preferably pH 3.8–4.2 and most preferably pH 3.9.

More specifically, the non-ionic surfactant is selected from the nonoxynol family. Specific examples of non-ionic surfactants that may be utilized include polyoxyethylene sorbitan monolaurate, polyoxyethylene sorbitan monooleate, polyoxyethylene sorbitan monostearate, octylphenol ethylene oxide, nonoxynol and mixtures thereof.

Buffering agents, commonly known to those skilled in the chemical arts, may be utilized to bring the pH of the composition to the desired range. Such buffering agents include any inorganic and organic bases and salts and their conjugate acids. Ammonium acetate and its conjugate acid are most preferred.

As described in greater detail below, the resulting substantially non-corrosive antimicrobial composition takes advantage of the best antimicrobial properties of iodophors and fatty acids. The unique chemistry of the composition prevents inactivation of the active agent by environmental contaminants and particularly those of organic origin. Further, the iodophor and fatty acid(s) function together to provide a synergistic beneficial effect resulting from an interaction of these materials that is described in greater detail below.

In accordance with still another aspect of the present invention, methods are provided for utilization of the compositions as antiseptics and disinfectants.

DETAILED DESCRIPTION OF THE INVENTION

As indicated above, the present invention is drawn to novel, substantially non-corrosive antimicrobial compositions. Advantageously, the compositions combine the antimicrobial activity of iodine and fatty acid(s) to obtain an enhanced microbicidal synergistic effect.

Specifically, the compositions have a resulting unique chemistry that substantially prevents inactivation of the active antimicrobial agents by environmental contaminants and particularly organic environmental contaminants. Through buffering, the composition is also made effectively non-corrosive. Further, the antimicrobial activity is effective against a wide range of microorganisms and is exhibited over a wide range of environmental conditions. Accordingly, the compositions have a wide range of industrial and institutional applications including utilization as a sanitizer, disinfectant and antiseptic. The unique chemistry and synergistic effect obtained is described in greater detail in the following discussion.

In accordance with the present invention the substantially noncorrosive antimicrobial compositions include by weight percent substantially 0.25–2.0% free iodine. Preferably, this available iodine is provided from an iodophor source. As is well known in the art, an iodophor includes surface active agents such as non-ionic surfactants, that act as carriers for solubilizing iodine. Iodine is a potent oxidizing agent that is known in the art to bring about irreversible damage to biological membranes of various microbial life forms. For example, iodine is known to oxidize tyrosine amino acid residues. Accordingly, iodine is known to effectively cause irreversible damage through oxidation of membrane proteins of various microbial life forms and thereby provide the desired antimicrobial action.

Many iodophor compositions are known in the art and commercially available. Such iodophors, utilizing nonoxynol-like compounds as carriers to provide a source of iodine include Bardyne I-20, Biopal CBL-10, Bio Surf I-20, Dermavine, Idonyx, Iobac, Ioprep, Iosan, Kleenodyne, Providine-Iodine, Rhudane, Showersan, Wescodyne and Westamine X.

Additionally, the present antimicrobial compositions include by weight percent between substantially 20.0 and 50.0% fatty acid or mixtures of fatty acids. Such fatty acids may be selected from a group including for example, formic acid, acetic acid, propionic acid, n-butyric acid, isobutyric acid, n-valeric acid, isovaleric acid, lactic acid and mixtures thereof. These fatty acids are known to have antimicrobial properties due to their ability to also interact with biological membranes.

While it should be appreciated that the antimicrobial activity of both iodine and fatty acid(s) is known, the present invention is believed to be the first time that these two components have been combined in an antimicrobial composition. Further, this novel combination has led to a surprising and completely unpredictable synergistic antimicrobial activity. In particular, as shown and demonstrated in detail in the examples that follow, the intermediates and compositions of the present invention exhibit significantly enhanced antimicrobial activity against an extremely wide range of organisms including bacteria, fungi and viruses. Further, this activity remains uncompromised in the presence of organic matter routinely found in the environment. No existing antimicrobial composition known to the inventors exhibits anything approaching this uncompromised, broad-spectrum germicidal activity in this pH range while also exhibiting little or no toxicity. As a result, the compositions of the present invention have far reaching applications and may in fact be utilized as a substitute for a number of different disinfectants, antiseptics, germicides or sanitizers of more organism-specific, destructive nature as are presently available in the marketplace.

The reason for the unique, powerful and wide ranging antimicrobial activity resulting from this novel combination is not yet fully understood. It is theorized, however, that the fatty acid(s) and iodine react to form complexes with a formula R-COOH:I. Alternatively, iodized fatty acid mixtures of indefinite composition are formed. In any event, the enhanced, wide ranging antimicrobial activity is real. The synergistic microbicidal activity, resulting in an enhanced degree and scope of action, is hypothesized to be due to enhanced interaction of the components with the biological membranes thereby causing rapid and irreversible damage.

The substantially noncorrosive antimicrobial compositions prepared in accordance with the present method also comprise by weight percent: between substantially 15.0–35.0% non-ionic surfactant. Specifically, additional non-ionic surfactant above the amount contained in the iodophor is added to the composition to bring the total weight percent of non-ionic surfactant within this desired range. As will be described in greater detail below, the additional non-ionic surfactant stabilizes the iodophor during addition of the buffering agent so as to prevent a loss of activity at the desired, less acidic and less corrosive pH range for the composition of between pH 3.0–5.0, more preferably pH 3.8–4.2 and most preferably pH 3.9.

In addition, the antimicrobial compositions of the present invention include between substantially 5.0–16.0% (w/v) buffering agent. As indicated above, the buffering agent is necessary to render the stabilized iodophor-fatty acid active agent intermediate substantially noncorrosive and therefore environmentally safe. In order to maintain the desired antimicrobial activity, it is necessary to buffer the iodophor-fatty acid intermediate to a pH value similar to the disassociation constants of the fatty acid(s) utilized in the composition. Accordingly, buffering is utilized to preferably bring the compositions to a pH of between 3.0 and 5.0. For example, a pH of approximately 3.9 is provided when utilizing a mixture of propionic and lactic acids.

As is known in the art, any inorganic and organic bases and salts and their conjugate acids may be utilized for buffering. Specific examples of various buffering agents are found throughout the literature. A representative list, presented as an example and not to be limited thereto includes: alanine, liquor ammonia, ammonium acetate, ammonium benzoate, ammonium bicarbonate, ammonium hydroxide, benzoic acid, beryllium hydroxide, calcium acetate, calcium carbonate, calcium hydroxide, calcium tartrate, deuteroammonium hydroxide, diethylamine, glutamic acid, hydrazine, hydroxylamine, magnesium acetate, magnesium benzoate, manganese carbonate, manganese sulfate, potassium acetate, potassium bicarbonate, potassium carbonate, potassium citrate, potassium hydroxide, potassium phosphate, quinine, quinoline, sodium acetate, sodium ascorbate, sodium bicarbonate, sodium bisulfate, sodium carbonate, sodium citrate, sodium hydroxide, sodium phosphate, silver hydroxide and zinc hydroxide with their conjugate acids/bases.

Of course, water may also be added to the antimicrobial composition during preparation. More specifically, water may be added directly into the stabilized iodine-fatty acid active agent intermediate or by adding to the buffering agent and then into the active agent intermediate. The composition may include between substantially 10.0–60.0% (v/v) water.

Further dilution with water may be made later to prepare an antiseptic, disinfectant or germicide of desired concentration for a particular application. Specifically the composition may be diluted to provide between 50–800 parts water to 1 part iodine-fatty acid active agent intermediate.

A particularly effective formulation of the present composition includes by weight percent substantially 1.7% available iodine, 25.0% propionic acid, 25.0% lactic acid, 21.6% non-ionic surfactant (i.e. 15.0% polyoxyethylene sorbitan monolaurate and 6.6% octylphenol ethylene oxide) and 15.54 gm ammonium acetate. Water may be added to this composition to provide a desired strength of antimicrobial activity for any particular application at hand.

As specifically shown in the following examples, the active agent intermediate may be prepared by mixing by weight percent substantially 0.25 to 2.0% available iodine from an iodophor with 20.0 to 50.0% fatty acid(s) in a mixing vessel. The mixing may be completed at approximately 25° C. The intermediate may next be diluted with water to bring it to the desired concentration or activity for any particular application. Alternatively, dilution with water may be made during addition of buffering agent or at time of use after preparation as described below.

The antimicrobial compositions may then be prepared by adding the appropriate amount of buffering agent. When preparing the composition, however, it should be appreciated that the addition of the buffering agent may result in a loss of some homogeneity, due to iodophor precipitation, and, accordingly, bactericidal efficacy, due to loss of free iodine. Thus, it is first necessary to ensure that sufficient carrier, such as a non-ionic surfactant, is present to stabilize the iodophor. The amount of non-ionic surfactant used is based on the amount of free iodine and the pH of the composition. Specifically, the amount of non-ionic surfactant in the composition may be adjusted based upon the amount of free iodine present and the type and amount of fatty acid(s) utilized to provide a total weight percent between 15.0 and 35.0%. The higher the concentration of free iodine and the higher the pH, the more non-ionic surfactant required.

Preferably, the non-ionic surfactant utilized is from the nonoxynol family. Specific non-ionic surfactants that may be utilized include polyoxyethylene sorbitan monolaurate, polyoxyethylene sorbitan monooleate, polyoxyethylene sorbitan monostearate, octylphenol ethylene oxide, nonoxynol and mixtures thereof. Commercially, available products that may be used for purposes of stabilization include, but are not limited to, Conco NI, Dowfax 9N, Igepal CO, Makon, Neutronyx 600's, Nonidet P40, Nonipol NO, Polytergent B, Renex 600's, Solar NP, Sterox, Surfonic N, T-DET-N, Tergitol NP, Triton N, Triton X-100, Tween 20, Tween 60 and Tween 80.

In order to provide an extended shelf-life for the antimicrobial composition, it has been found that a mixture of two or more different non-ionic surfactants is preferred. One particularly useful mixture for this purpose is polyoxyethylene sorbitan monolaurate and octylphenol ethylene oxide in a ratio between 2:1 and 3:1 and more preferably 2.275:1.

Accordingly, preparation of the antimicrobial compositions of the present invention is completed by adding the appropriate amount of non-ionic surfactant to the iodine-fatty acid active agent intermediate and then adding the buffer. Alternatively, the buffer is added to non-ionic surfactant and then this preparation is added to the iodine-fatty acid active agent intermediate.

After preparation, the antimicrobial composition may be diluted to a desired concentration or working strength for a particular application. More specifically, the composition may be diluted to a total of between substantially 50–800 parts water to 1 part iodine-fatty acid(s) active agent intermediate.

The following examples are to further illustrate the invention but it is not to be considered as limited thereto.

EXAMPLE 1

In a stainless steel mixing vessel, 0.83 ml of an iodophor, Bio Surf I-20 (providing 20% titratable iodine, 1.25% (w/v)), is carefully blended by constant stirring into a mixture of 10.0 ml of propionic acid and 10.2 gm of lactic acid at 25° C. until dissolved. Next 15.5 ml of polyoxyethylene sorbitan monolaurate is added to the iodophor and fatty acid mixture by constant stirring at 25° C. An aqueous buffer solution is then prepared by adding 5.8 gm of ammonium acetate to a final volume of 63.7 ml water. This aqueous buffer solution is then slowly added to the stabilized iodine-fatty acids active agent intermediate by constant stirring also at 25° C. The resulting formulation after mixing all the ingredients has an effective pH between 3.8 and 4.0 and 0.25% available iodine.

EXAMPLE 2

In a glass lined mixing vessel, 1.7 ml of iodophor (Bio Surf I-20 providing 20% titratable iodine, 2.5% (w/v)), is carefully blended by constant stirring into a mixture of 10.0 ml of propionic acid and 10.2 gm of lactic acid at 25° C. until dissolved. The resulting active agent intermediate is then stabilized by adding 17.0 ml of polyoxyethylene sorbitan monostearate and blending slowly to homogeneity by constant stirring at 25° C. A buffer solution is then separately prepared by dissolving 6.0 gm of ammonium acetate to achieve a final volume of 61.3 ml of water. After dissolving the ammonium acetate, the buffer solution is then added to the stabilized iodine-fatty acid(s) intermediate while stirring continues to obtain a buffered, stabilized homogenate. The resulting composition has an effective pH of between 3.8 and 4.0 and 0.5% available iodine.

EXAMPLE 3

In a glass lined mixing vessel, 3.3 ml of iodophor (Bio Surf I-20 providing 20% titratable iodine, 5.0% (w/v)), is carefully blended by constant stirring into a mixture of 10.0 ml of propionic acid and 10.2 gm of lactic acid at 25° C. until dissolved. The resulting active agent intermediate is then stabilized by adding 17.0 ml of polyoxyethylene sorbitan monooleate and blending slowly to homogeneity by constant stirring at 25° C. A buffer solution is then separately prepared by dissolving 6.4 gm of ammonium acetate to a final volume of 59.7 ml of water. This buffer solution is then added to the stabilized iodine-fatty acids intermediate while stirring continues to obtain a buffered, stabilized homogenate. The resulting composition has an effective pH of between 3.8 and 4.0 and 1.0% available iodine.

EXAMPLE 4

In a glass lined mixing vessel, 6.7 ml of iodophor (Bio Surf I-20 providing 20% titratable iodine, 2% (w/v)), is carefully blended by constant stirring into mixture of 10.0 ml of propionic acid and 10.2 gm of lactic acid at 25° C. until dissolved. The resulting active agent intermediate is then stabilized adding 15.0 ml of polyoxyethylene sorbitan monolaurate and 6.0 ml of octylphenol ethylene oxide and blending slowly to homogeneity by constant stirring at 25°

C. A buffer solution is then separately prepared by dissolving 8.3 gm of ammonium acetate to a final volume of 52.3 ml of water. The buffer solution is then added to the stabilized iodine-fatty acids intermediate while stirring continues to obtain a buffered, stabilized homogenate. The resulting composition has an effective pH of between 3.8 and 4.0 and 2.0% available iodine.

EXAMPLE 5

In a glass lined mixing vessel, 0.83 ml of iodophor (Bio Surf I-20 providing 20% titratable iodine, 1.25% (w/v)), is carefully blended by constant stirring into a mixture of 20.0 ml of propionic acid and 20.3 gm of lactic acid at 25° C. until dissolved. The resulting active agent intermediate is then stabilized by adding 26.0 ml of polyoxyethylene sorbitan monolaurate and 9.0 ml of octylphenol ethylene oxide and blending slowly to homogeneity by constant stirring at 25° C. 11.3 gm of ammonium acetate dissolved to achieve a final volume of 24.2 ml in water are then added to the stabilized iodine-fatty acids intermediate while stirring continues to obtain a buffered, stabilized homogenate.

EXAMPLE 6

In a glass lined mixing vessel, 1.7 ml of iodophor (Bio Surf I-20 providing 20% titratable iodine, 2.5% (w/v)), is carefully blended by constant stirring into a mixture of 20.0 ml of acetic acid and 20.0 ml of formic acid (88% assay). The resulting active agent intermediate is then stabilized by adding 30.0 ml of polyoxyethylene sorbitan monostearate and 5.0 ml of polyoxyethylene monolaurate blending slowly to homogeneity by constant stirring at 25° C. 15.6 gm of ammonium acetate dissolved to a final volume of 23.3 ml in water are then added to the stabilized iodine-fatty acids intermediate while stirring continues to obtain a buffered, stabilized homogenate.

EXAMPLE 7

In a glass lined mixing vessel, 0.83 ml of iodophor (Bio Surf I-20 providing 20% titratable iodine, 1.25% (w/v)), is carefully blended by constant stirring into a mixture of 10.0 ml of propionic acid and 10.0 ml of formic acid (88% assay) at 25° C. The resulting active agent intermediate is then stabilized by adding 8 ml of polyoxyethylene sorbitan monolaurate and blending slowly to homogeneity by constant stirring at 25° C. A buffer solution is prepared by dissolving 5.8 gm of ammonium acetate to achieve a final volume of 63.7 ml in water. The buffer solution is then added to the stabilized iodine-fatty acids intermediate while stirring continues to obtain a buffered, stabilized homogenate.

EXAMPLE 8

In a glass lined mixing vessel, 1.7 ml of iodophor (Bio Surf I-20 providing 20% titratable iodine, 2.5% (w/v)), is carefully blended by constant stirring into a mixture of 10.0 ml of acetic acid and 10.0 ml of formic acid (88% assay) at 25° C. The resulting active agent intermediate is then stabilized by adding 8.5 ml of polyoxyethylene sorbitan monolaurate and 6.5 ml of octylphenol ethylene oxide and blending slowly to homogeneity by constant stirring at 25° C. 6.0 gm of ammonium acetate was dissolved to achieve a final volume of 61.3 ml in water are then added while stirring continues to obtain a buffered, stabilized homogenate.

EXAMPLE 9

In a glass-lined mixing vessel, 0.83 ml of iodophor (Bio Surf I-20 providing 20% titratable iodine, 1.25% (w.v)), is carefully blended by constant stirring into 20.0 ml of propionic acid and 20.0 ml of formic acid (88% assay) at 25° C. The resulting active agent intermediate is then mixed with 14.0 ml of polyoxyethylene sorbitan monolaurate, 5.0 ml of octylphenol ethylene oxide, 15.2 gm of ammonium acetate dissolved to a final volume of 40.2 ml in water.

EXAMPLE 10

In a glass-lined mixing vessel, 0.83 ml of iodophor (Bio Surf I-20, 1.25% (w.v)), is carefully blended by constant stirring with 20 ml of propionic acid at 25° C. The resulting active agent intermediate is then mixed with 15.6 ml of polyoxyethylene sorbitan monolaurate and 7.8 gm of ammonium acetate dissolved to a final volume of 63.57 ml in water.

EXAMPLE 11

In a glass-line mixing vessel, 10.83 ml of iodophor complex containing 0.25% free iodine are carefully blended by constant stirring into 10.0 ml of acetic acid, 20.0 ml of propionic acid, 20.3 gm of lactic acid and 15 ml of octylphenol ethylene oxide. The resulting active agent intermediate is then mixed with 5.0 ml of liquor ammonia and 19.17 ml of water.

EXAMPLE 12

In a glass-lined mixing vessel, 10.83 ml of iodophor complex containing 0.25% free iodine are carefully blended by constant stirring into 40.0 ml of propionic acid. The resulting active agent intermediate is then mixed to homogeneity with 16.5 ml of polyoxyethylene sorbitan monolaurate, 6.0 ml of octylphenol ethylene oxide, 2.0 grams of calcium hydroxide ($Ca(OH)_2$) and 26.67 ml of water.

EXAMPLE 13

In a stainless steel mixing vessel, 5.7 ml of iodophor, Bio Surf I-20, containing 1.7% free iodine is carefully blended by constant stirring into a mixture of 15.0 ml propionic acid and 15.3 gm of lactic acid at 25° C. until dissolved. Next, 15.0 ml of polyoxyethylene sorbitan monolaurate and 6.6 ml of octylphenol ethylene oxide is added to the iodophor and fatty acid intermediate with constant stirring at 25° C. 13.3 gm of ammonium acetate dissolved to a final volume of 42.7 ml in water is then slowly added to the stabilized iodine-fatty acid intermediate by constant stirring also at 25° C.

EXAMPLE 14

In a stainless steel mixing vessel, 5.7 ml of iodophor, Bio Surf I-20, containing 1.7% free iodine is carefully blended by constant stirring into a mixture of 20.0 ml propionic acid and 20.3 gm of lactic acid at 25° C. until dissolved. Next, 15.0 ml of polyoxyethylene sorbitan monolaurate, 6.6 ml of octylphenol ethylene oxide, 12.6 gm of ammonium acetate dissolved to a final volume of 32.7 ml in water is mixed together in a separate vessel. This mixture is then slowly added to the stabilized iodine fatty acid intermediate by constant stirring also at 25° C.

EXAMPLE 15

In a stainless steel mixing vessel, 5.7 ml of iodophor, Bio Surf I-20, containing 1.7% free iodine is carefully blended by constant stirring into a mixture of at 25.0 ml propionic acid and 25.4 gm of lactic acid at 25° C. until dissolved. Next, 25.0 ml of polyoxyethylene sorbitan monolaurate, 6.6 ml of octylphenol ethylene oxide, 15.4 gm of ammonium acetate dissolved to obtain a final volume of 12.7 ml in water are mixed together in a separate vessel. This mixture is then slowly added to the stabilized iodine-fatty acid intermediate by constant stirring also at 25° C.

EXAMPLE 16

In a stainless steel mixing vessel, 6.3 ml of iodophor, Bio Surf I-20, containing 1.7% titratable iodine is carefully blended by constant stirring into a mixture of 25.0 ml propionic acid and 25.4 gm of lactic acid at 25° C. until dissolved. Next, 15.0 ml of polyoxyethylene sorbitan monolaurate, 6.6 ml of octylphenol ethylene oxide and 15.5 gm of ammonium acetate dissolved to a final volume of 21.0 ml in water are mixed together in a separate vessel. This mixture is then slowly added to the stabilized iodine-fatty acid intermediate by constant stirring also at 25° C.

EXAMPLE 17

The antibacterial activity of the composition of the present invention prepared in accordance with Example 16 was compared with a number of biocide products presently available in the marketplace including Sal-Zap, Bio Surf and Wescodyne. Specifically, a gram negative bacterial culture was diluted to a final concentration of $2.5-3.0 \times 10^6$ cells/ml and treated with the indicated biocide for an exposure time of 1 minute and 5 minutes. Treated cells were then transferred to recovery medium and allowed to incubate for the indicated time periods. Growth in the recovery medium was recorded as + (growth) or − (no growth). Table 1 indicating the results is set forth below.

TABLE 1

| Biocide | Ex-posure Time | \multicolumn{7}{c}{Time After Transfer to Recovery Medium (hrs)} | | | | | | |
|---|---|---|---|---|---|---|---|---|
| | | 12 | 24 | 36 | 48 | 72 | 96 | 120 |
| Sal-Zap | 5 min | ++ | ++ | ++ | ++ | ++ | ++ | ++ |
| | 1 min | ++ | ++ | ++ | ++ | ++ | ++ | ++ |
| Bio Surf | 5 min | ++ | ++ | ++ | ++ | ++ | ++ | ++ |
| | 1 min | ++ | ++ | ++ | ++ | ++ | ++ | ++ |
| Wescodyne | 5 min | ++ | ++ | ++ | ++ | ++ | ++ | ++ |
| | 1 min | ++ | ++ | ++ | ++ | ++ | ++ | ++ |
| Antimicrobial Composition of Example 16 | 5 min | − | − | − | − | − | − | − |
| | 1 min | − | − | − | − | − | − | − |

The above results are shown for bacteria exposed to the indicated biocide in the presence of 5% fetal calf serum. Clearly, the antimicrobial composition of the present invention displays significantly enhanced activity against gram negative bacteria over that displayed by commercially available products in an environment including organic matter (i.e. fetal calf serum).

EXAMPLE 18

The antibacterial activity of the composition of the present invention prepared in accordance with Example 16 was shown. Specifically, a broad spectrum of gram positive and gram negative bacteria was isolated from raw milk on blood agar. Cells from isolated colonies were then suspended in tap water plus 5% (v/v) fetal calf serum (FCS) and treated with the present antimicrobial composition (1 to 100 dilution) for ten minutes at room temperature. 100 µl of treated cells were then transferred aseptically to 5 ml of a recovery medium (buffered peptone+M9 salts) and incubated at room temperature. The tubes were then examined for growth after 24 and 48 hours. At the end of the 48 hour incubation period, 50 µl of recovery medium from each treated culture was plated out on Luria-Bertani (LB) agar and examined for colonies after an additional incubation period at room temperature of 24 and 48 hours. Untreated cells were passed through the same steps (excluding treatment with the antimicrobial composition) to provide positive controls. Cells from the LB agar were gram stained and examined microscopically under oil immersion. The results are shown in Table 2 below ("−" indicates no growth; "+" indicates growth):

TABLE 2

| Bacteria | Incubation period | Growth after 10 minute treatment in | | Growth in LB agar |
|---|---|---|---|---|
| | | 5% FCS | 10% M | |
| Encapsulated, beta-hemolytic Streptococcus | 24 hr 48 hr | − − | − − | − − |
| Listeria sp. | 24 hr 48 hr | − − | − − | − − |
| Non-hemolytic Streptococcus | 24 hr 48 hr | − − | − − | − − |
| Unidentified Gram positive | 24 hr 48 hr | − − | − − | − − |
| Unidentified Gram negative (pleomorphic) | 24 hr 48 hr | − − | − − | − − |
| Unidentified Gram negative rod | 24 hr 48 hr | − − | − − | − − |
| Controls | 24 hr 48 hr | + +++ | + +++ | + +++ |

EXAMPLE 19

The antifungal activity of the composition of the present invention prepared in accordance with Example 16 was shown. Specifically strawberries on which Aspergillus sp. was growing were crushed and then incubated for several days until the strawberry juice was turbid. 5 ml of the turbid juice was then treated with a 1:256 dilution of the antimicrobial composition at room temperature for 30 minutes. Next the treated juice was diluted 1:50 with water and 1–2 ml of the diluted juice was mixed with a dried cornmeal and milk medium. The mixture was allowed to air-dry and then placed into a plastic bag and incubated at room temperature. 1–2 ml of untreated, diluted juice was also mixed with a sample of the dried corn meal and milk medium, air dried, placed into a separate plastic bag and incubated at room temperature (positive control). The results ("−" indicating no growth, "+" indicates growth) are presented in Table 3 below:

TABLE 3

| End-of-week | Growth of Aspergillus | |
| --- | --- | --- |
| | Treated Juice | Untreated Juice |
| 1 | – | + |
| 2 | – | ++ |
| 3 | – | +++ |
| 4 | + | ++++[a] |

[a] dried corn meal and milk medium completely covered by fungi

EXAMPLE 20

Another comparative study was made to demonstrate the enhanced antimicrobial activity and beneficial synergistic effect of the composition of the present invention relative to the antimicrobial activity of iodine alone and various fatty acid alone. Specifically, the procedure outlined in example 17 was followed with the following results:

TABLE 4

| Biocide | Exposure Time | Time After Transfer to Recovery Medium (hrs) | | | | | | |
| --- | --- | --- | --- | --- | --- | --- | --- | --- |
| | | 12 | 24 | 36 | 48 | 72 | 96 | 120 |
| Iodine 80 ppm | 5 min | ++ | ++ | ++ | ++ | ++ | ++ | ++ |
| | 1 min | ++ | ++ | ++ | ++ | ++ | ++ | ++ |
| Propionic Acid 0.04% | 5 min | ++ | ++ | ++ | ++ | ++ | ++ | ++ |
| | 1 min | ++ | ++ | ++ | ++ | ++ | ++ | ++ |
| Lactic Acid 0.0375% | 5 min | ++ | ++ | ++ | ++ | ++ | ++ | ++ |
| | 1 min | ++ | ++ | ++ | ++ | ++ | ++ | ++ |
| Propionic Acid (0.04%) and Lactic Acid (0.0375%) | 5 min | – | – | + | ++ | ++ | ++ | ++ |
| | 1 min | – | + | ++ | ++ | ++ | ++ | ++ |
| Antimicrobial Composition of Example 16 1:250 | 5 min | – | – | – | – | – | – | – |
| | 1 min | – | – | – | – | – | – | – |

EXAMPLE 21

The corrosive activity of the composition of the present invention prepared in accordance with Example 16 was evaluated. Specifically, a 1:256 diluted solution of the composition was placed on samples of stainless steel and aluminum for a period of 24 and 36 hours. The solutions were then washed off and the metal was examined under magnification for indications of corrosion. No observable signs of corrosion of the metals were found when examined under magnification. Rubber O-rings were also allowed to soak in a 1:256 diluted solution of the composition for 24 hours and then examined under magnification. No observable cracking of the rubber when stretched or bent double were found when examined under magnification.

In application, the composition of the present invention may be utilized as either a disinfectant on inanimate objects or an antiseptic on living tissue. Advantageously, the antimicrobial composition of the present invention approaches an ideal formulation as it has wide ranging activity against bacteria, fungi and viruses under a wide range of environmental conditions. It is also buffered so as to be substantially non-corrosive and advantageously does not tend to stain or discolor materials on which it is utilized.

Accordingly, a method for disinfecting a surface of an inanimate object includes the step of applying to said surface an effective amount of the antimicrobial composition. Similarly, a method for killing microorganisms on living tissue includes a step of applying to said living tissue an effective amount of the antimicrobial composition.

We claim:

1. An antimicrobial composition, comprising by weight percent:
   0.25–2.0% available iodine;
   20.0–50.0% fatty acid;
   15.0–35.0% non-ionic surfactant;
   5.0–16.0% (w/v) buffering agent; and
   10.0–60.0% (v/v) water, and having a pH between 3.0 and 5.0.

2. An antimicrobial composition, comprising by weight percent:
   0.25–2.0% available iodine;
   20.0–50.0% fatty acid;
   15.0–35.0% non-ionic surfactant;
   5.0–16.0% (w/v) buffering agent; and
   10.0–60.0% (v/v) water, and having a pH between 3.8 and 4.2.

3. An antimicrobial composition, comprising by weight percent:
   0.25–2.0% available iodine;
   20.0–50.0% fatty acid;
   15.0–35.0% non-ionicsurfactant;
   5.0–16.0% (w/v) buffering agent; and
   10.0–60.0% (v/v) water, and having a pH of substantially 3.9.

4. The antimicrobial composition set forth in claim 1, wherein said fatty acid is selected from a group consisting of formic acid, acetic acid, propionic acid, n-butyric acid, isobutyric acid, n-valeric acid, isovaleric acid, lactic acid and mixtures thereof.

5. The antimicrobial composition set forth in claim 4, wherein said non-ionic surfactant is a nonoxynol.

6. The antimicrobial composition set forth in claim 5, wherein said buffering agent is selected from a group consisting of alanine, liquor ammonia, ammonium acetate, ammonium benzoate, ammonium bicarbonate, ammonium hydroxide, benzoic acid, beryllium hydroxide, calcium acetate, calcium carbonate, calcium hydroxide, calcium tartrate, deuteroammonium hydroxide, diethylamine, glutamic acid, hydrazine, hydroxylamine, magnesium acetate, magnesium benzoate, manganese carbonate, manganese sulfate, potassium acetate, potassium bicarbonate, potassium carbonate, potassium citrate, potassium hydroxide, potassium phosphate, quinine, quinoline, sodium acetate, sodium ascorbate, sodium bicarbonate, sodium bisulfate, sodium carbonate, sodium citrate, sodium hydroxide, sodium phosphate, silver hydroxide, zinc hydroxide and mixtures thereof with their conjugate acids/bases.

7. The antimicrobial composition set forth in claim 1, wherein said non-ionic surfactant is a nonoxynol.

8. The antimicrobial composition set forth in claim 1, wherein said buffering agent is selected from a group consisting of alanine, liquor ammonia, ammonium acetate, ammonium benzoate, ammonium bicarbonate, ammonium hydroxide, benzoic acid, beryllium hydroxide, calcium acetate, calcium carbonate, calcium hydroxide, calcium tartrate, deuteroammonium hydroxide, diethylamine, glutamic acid, hydrazine, hydroxylamine, magnesium acetate, magnesium benzoate, manganese carbonate, manganese sulfate, potassium acetate, potassium bicarbonate, potassium carbonate, potassium citrate, potassium hydroxide, potassium phosphate, quinine, quinoline, sodium acetate, sodium ascorbate, sodium bicarbonate, sodium bisulfate, sodium carbonate, sodium citrate, sodium hydroxide, sodium phosphate, silver hydroxide, zinc hydroxide and mixtures thereof with their conjugate acids/bases.

9. The antimicrobial composition set forth in claim 1, wherein said non-ionic surfactant is selected from a group consisting of polyoxyethylene sorbitan monolaurate, polyoxyethylene sorbitan monooleate, polyoxyethylene sorbitan monostearate, octylphenol ethylene oxide, nonoxynol and mixtures thereof.

10. The antimicrobial composition set forth in claim 9, wherein said buffering agent is ammonium acetate and its conjugate acid.

11. The antimicrobial composition set forth in claim 1, wherein said antimicrobial composition is further diluted with water to provide between 50–800 parts water to 1 part iodine and fatty acid.

12. A method for disinfecting a surface of an inanimate object, comprising:

applying to the surface of on inanimate object an effective amount of the antimicrobial composition set forth in claim 1.

13. A method for killing microorganisms on living tissue, comprising:

applying to living tissue an effective amount of the antimicrobial composition set forth in claim 1.

14. An antimicrobial composition, consisting essentially of by weight percent:

0.25–2.0% available iodine;

20.0–50.0% fatty acid;

15.0–35.0% non-ionic surfactant consisting of a mixture of polyoxyethlyene sorbitan monolaurate and octylphenol ethylene oxide;

5.0–16.0% (w/v) buffering agent; and 10.0–60.0% (v/v) water, and having a pH of 3.8–4.2.

15. The antimicrobial composition set forth in claim 14 wherein said fatty acid is a mixture of 25.0% propionic acid and 25.0% lactic acid.

16. The antimicrobial composition set forth in claim 15, wherein said buffering agent is 15.54% ammonium acetate.

17. The antimicrobial composition set forth in claim 15, wherein said polyoxyethylene sorbitan monolaurate and octylphenol ethylene oxide are provided at a ratio between 2:1 to 3:1.

* * * * *